United States Patent
Weinstein et al.

(10) Patent No.: US 6,190,903 B1
(45) Date of Patent: Feb. 20, 2001

(54) BACTERIA HAVING ATCC NO. 55926 OR ATCC NO. 202050 CAPABLE OF BIODEGRADATION OF WASTES

(75) Inventors: I. Bernard Weinstein, Engelwood; David Figurski, Dumont, both of NJ (US); Sadayori Hoshina, Tokyo (JP); Koji Nakanishi, New York, NY (US)

(73) Assignee: The Trustees of Columbia University in the City of New York, New York, NY (US)

( * ) Notice: Under 35 U.S.C. 154(b), the term of this patent shall be extended for 0 days.

(21) Appl. No.: 08/979,586

(22) Filed: Nov. 26, 1997

(51) Int. Cl.⁷ ................ B09B 3/00; C12N 1/00; C12N 1/20; D06M 16/00
(52) U.S. Cl. ............. 435/252.5; 435/261; 435/262.5; 435/264; 435/832
(58) Field of Search ................ 435/252.5, 261, 435/262.5, 264, 832

(56) References Cited

U.S. PATENT DOCUMENTS

| 5,610,061 | 3/1997 | Pierce | 435/252.1 |
| 5,736,032 | * 4/1998 | Cox et al. | 424/76.5 |
| 5,783,431 | * 7/1998 | Peterson et al. | 435/172.3 |

OTHER PUBLICATIONS

Cabirol, N., et al., (1996) "Role of Methanogenic and Sulfate–Reducing Bacteria in the Reductive Dechlorination of Tetrachloroethylene in Mixed Culture." *Bull Environ Contam Toxicol* 56: 817–824.

Deshusses, Marc, A., (1997) "Biological Waste Ait Treatment in Biofilters." *Biotechnology* 8 (3):335–339.

Gisi, D., Stucki, G., Hanselmann, W., (1997) "Biodegradation of the Pesticide 4, 6–dinitro–ortho–cresol by Microorganisms in Batch Cultures and in Fixed–bed Column Reactors." *Appl Microbiol Biotechnol* 48:441–448.

* cited by examiner

*Primary Examiner*—David M. Naff
*Assistant Examiner*—Deborah K. Ware
(74) *Attorney, Agent, or Firm*—John P. White; Cooper & Dunham LLP

(57) ABSTRACT

A biologically pure culture of a microorganism is provided designated SH2A and deposited under ATCC Accession No. 55926, or a mutant derived therefrom. Further provided is a biologically pure culture of a microorganism designated SH2B and deposited under ATCC Accession No. 202050, or a mutant derived therefrom. A method of degrading an organic material is carried out by treating the organic material with an effective, degrading amount of either SH2A or a mutant derived therefrom, or SH2B or a mutant derived therefrom. The microorganism designated SH2A or a mutant derived therefrom, or SH2B or a mutant derived therefrom, is grown by culturing the microorganism at a temperature and in a medium effective to promote growth of the microorganism.

26 Claims, 1 Drawing Sheet

Fig. 1

Sequence of 16S rRNA

GCGACGTTGTCCGGAATTATTGGGCGTAAAGCGCGCG
AGGCGGTCCTTTAAGTCTGATGTGAAAGCCCACGGCTC
AACCGTGGAGGGTCATTGGAAACTGGGGGACTTGAGTG
CAGGAGAGGAGAGCGGAATTCCACGTGTAGCGGTGAAA
TGCGTAGAGATGTGGAGGAACACCAGTGGCGAAGGCGG
CTCTCTGGCCTGTAACTGACGCTGAGGCGCGAAAGCGT
GGGGAGCAAACAGGATTAGATACCCTGGTAGTCCACGC
CGTAAACGATGAGTGCTAAGTGTTAGAGGGGTCACACC
CTTTAGTGCTGTAGCTAACGCGATAAGCACTCCGCCTG
GGGAGTACGGCCGCAAGGCTGAAACTCAAAGGAATTGA
CGGGGGCCCGCACAAGCGGTGGAGCATGTGGTTTAATT
CGAAGCAACGCGAAGAACCTTACCAGGTCTTGACATCC
CCTGACAACCCAAGAGATTGGGCGTTCCCCTTCCGGG
GGACAAGGTGACACGTGGTGCATGGTTGTCTTCACCTC
GTTCTT

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: other nucleic acid (iii) HYPOTHETICAL: NO -continued (iv) ANTI-SENSE: NO (xi) SEQUENCE DESCRIPTION: SEQ ID NO:1:

CAGCAGCCGC GGTAATAC                                                       18

(2) INFORMATION FOR SEQ ID NO:2:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:2:

GATTAGATAC CCTGGTA                                                        17

(2) INFORMATION FOR SEQ ID NO:3:

(i) SEQUENCE CHARACTERISTICS:
        (A) LENGTH: 538 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:3:

GCGACGTTGT CCGGAATTAT TGGGCGTAAA GCGCGCGCAG GCGGTCCTTT AAGTCTGATG    60

TGAAAGCCCA CGGCTCAACC GTGGAGGGTC ATTGGAAACT GGGGGACTTG AGTGCAGGAG   120

AGGAGAGCGG AATTCCACGT GTAGCGGTGA AATGCGTAGA GATGTGGAGG AACACCAGTG   180

GCGAAGGCGG CTCTCTGGCC TGTAACTGAC GCTGAGGCGC GAAAGCGTGG GGAGCAAACA   240

GGATTAGATA CCCTGGTAGT CCACGCCGTA AACGATGAGT GCTAAGTGTT AGAGGGGTCA   300

CACCCTTTAG TGCTGTAGCT AACGCGATAA GCACTCCGCC TGGGGAGTAC GGCCGCAAGG   360

CTGAAACTCA AAGGAATTGA CGGGGGCCCG CACAAGCGGT GGAGCATGTG GTTTAATTCG   420

AAGCAACGCG AAGAACCTTA CCAGGTCTTG ACATCCCCTG ACAACCCAAG AGATTGGGCG   480

TTCCCCCTTC CGGGGACAA GGTGACACGT GGTGCATGGT TGTCTTCACC TCGTTCTT      538

BACTERIA HAVING ATCC NO. 55926 OR ATCC NO. 202050 CAPABLE OF BIODEGRADATION OF WASTES

BACKGROUND

Human industrial activities inevitably generate industrial wastes. These industrial wastes primarily consist of inorganic and organic waste discharged by factories, agriculture, fisheries and food processing industries. The high cost of degrading or handling these wastes are borne by these industries. These costs hinder market expansion for these and other related businesses.

Currently, organic waste fermentation and treatment systems have been developed for utilizing waste. Using these systems, one can currently produce biologically active substances such as soil improvement agents, and compost.

It would be useful to manufacture and market a biomass fermentation and treatment method capable of converting wastes produced by fisheries, and vegetable and animal bioprocessing industries into biologically responsive modifiers, animal feed, fertilizer or fermentation agents. Such a method would include a system for treating waste and a new fermentation agent that would be useful in waste decomposition. Using such a system, one would be able to 1) reduce waste treatment costs, 2) prevent pollution of the environment, 3) improve soil, e.g. farmlands, and 4) yield biologically active reuseable substances.

Accordingly, applicants sought a new bacterium capable of degrading lipids, proteins, carbohydrates, and wood fiber. Such a bacterium could be useful for many different purposes it biodegradation of waste. This new system of biodegradation would be capable of targeting different types of waste and broadening the applicability of waste degradative methods.

Applicants concentrated on thermophilic bacteria due to their rapid growth. Also, thermophilic bacteria are considered by many in the field to be the safest and most effective bacterium for use in bioprocessing procedures.

Thermophilic bacteria are an ideal choice for the following reasons because they are:

1) well studied/characterized;
2) aerobic;
3) capable of being manipulated for recombinant DNA purposes;
4) able to grow at a specific optimum high temperature;
5) capable of stably maintaining introduced foreign genes; and
6) efficient and predictable expression of introduced exogenous genes to produce exogenous proteins.

SUMMARY OF THE INVENTION

This invention provides a biologically pure culture of a microorganism designated SH2A and deposited under ATCC Accession No. 55926, or a mutant derived therefrom. This invention further provides a biologically pure culture of a microorganism designated SH2B and deposited under ATCC Accession No. 202050, or a mutant derived therefrom.

This invention provides a method of degrading an organic material which comprises treating the organic material with an effective, degrading amount of a microorganism designated SH2A and deposited under ATCC Accession No. 55926, or a mutant derived therefrom which retains the degrading activity thereof, so as to thereby degrade the material.

This invention further provides a method of degrading an organic material which comprises treating the organic material with an effective, degrading amount of a microorganism designated SH2B and deposited under ATCC Accession No. 202050, or a mutant derived therefrom which retains the degrading activity thereof, so as to thereby degrade the material.

This invention also provides a method for growing a microorganism designated SH2A and deposited under ATCC Accession No. 55926, or a mutant derived therefrom, which comprises culturing the microorganism at a temperature and medium effective to promote growth of the microorganism.

This invention also provides a method for growing a microorganism designated SH2B and deposited under ATCC Accession No. 202050, or a mutant derived therefrom, which comprises culturing the microorganism at a temperature and medium effective to promote growth of the microorganism.

BRIEF DESCRIPTION OF THE FIGURES

FIG. 1. Nucleic acid sequence of the bacterium strain SH2A and SH2B 16S rRNA.

DETAILED DESCRIPTION OF THE INVENTION

Throughout this application, references to specific nucleotides are to nucleotides present on the coding strand of the nucleic acid. The following standard abbreviations are used throughout the specification to indicate specific nucleotides:

| C = cytosine | A = adenosine |
| T = thymidine | G = guanosine |

As used herein "aerobic" means pertaining to or requiring oxygen.

The present invention provides for a biologically pure culture of a microorganism designated SH2A and deposited under ATCC Accession No. 55926, or a mutant derived therefrom.

Bacterium strain, Bacillus midousuji SH2A was deposited on Jan. 21, 1997 with the American Type Culture Collection (ATCC), 12301 Parklawn Drive, Rockville, Md. 20852, U.S.A., under the provisions of the Budapest Treaty For The International Recognition Of The Deposit Of Microorganisms For The Purposes Of Patent Procedure. Bacterium strain SH2A has been accorded ATCC Accession No. 55926.

This invention further provides a biologically pure culture of a microorganism designated SH2B and deposited under ATCC Accession No. 202050, or a mutant derived therefrom.

Bacterium strain, Bacillus midousuji SH2B was deposited on Oct. 24, 1997 with the American Type Culture Collection (ATCC), 12301 Parklawn Drive, Rockville, Md. 20852, U.S.A., under the provisions of the Budapest Treaty For The International Recognition Of The Deposit Of Microorganisms For The Purposes Of Patent Procedure. Bacterium strain SH2B has been accorded ATCC Accession No. 202050.

This invention further provides a method of degrading an organic material which comprises treating the organic material with an effective, degrading amount of a microorganism designated SH2A and deposited under ATCC Accession No. 55926, or a mutant derived therefrom which retains the degrading activity thereof, so as to thereby degrade the material.

Determination of "an effective, degrading amount of microorganism" as described in the claimed invention is within the knowledge of one skilled in the art. Various methods exist in which one can determine the amounts of the bacteria required to effectively degrade the waste of interest.

This invention further provides a method of degrading an organic material which comprises treating the organic material with an effective, degrading amount of a microorganism designated SH2B and deposited under ATCC Accession No. 202050, or a mutant derived therefrom which retains the degrading activity thereof, so as to thereby degrade the material The organic material degraded by the bacterial strains above include, but should not be limited to, plastics, specifically polyethylene. In one specific embodiment, the polyethylene may be irradiated prior to treatment with the bacterial strains to facilitate the degradative process. Specifically, in such an embodiment, the polyethylene may be irradiated with ultra-violet light.

The organic material degraded by the bacterial strains above may also comprise a protein, specifically waste products of households and such industries as food-processing, agriculture, dairy or fisheries. Specific examples include, but are not limited to, wood pulp, paper products, shellfish, coffee bean dregs, tunafish heads, squids and other by-products of these industries. Further kitchen waste may also be degraded by these bacteria. Kitchen waste may include, but are not limited to, paper products, shellfish, coffee bean dregs, tunafish heads, squids and other by-products found in kitchen bins, trash dumps and other consumer-based waste.

This invention further provides wherein organic material comprising a sugar is degraded by the methods described above. Specifically such sugars include, but are not limited to, mannose, maltose, trehalose, fructose and raffinose. Many of these sugars may be found in kitchen wastes and are by-products of industries in food-processing and agriculture, e.g. fruits.

The organic material also includes amino acid-based compounds. These compounds may be proteins, polypeptides, peptides, naturally occurring or synthetic.

The organic material may also include a nucleic acid molecule, specifically deoxyribonucleic acid molecules. DNAse activity has been detected in these bacterial strains.

The above-identified methods can be effected at a temperature from about 62° C. to about 100° C. Specifically, the optimal growth temperature of the bacterial strains has been about 62° C.; however, the bioprocessing may take place at higher temperature. One skilled in the art would be capable of determining the optimal temperature for degrading material using these bacterial strains.

The above-identified methods can be effected at a pH at about 5.0 to about 8.0, specifically the pH is at about 7.4.

Further, these bacterial strains can be used in the above-identified methods in an aerobic environment.

This invention further provides a method for growing a microorganism designated SH2A and deposited under ATCC Accession No. 55926, or a mutant derived therefrom, which comprises culturing the microorganism at a temperature and medium effective to promote growth of the microorganism.

This invention further provides a method for growing a microorganism designated SH2B and deposited under ATCC Accession No. 202050, or a mutant derived therefrom, which comprises culturing the microorganism at a temperature and medium effective to promote growth of the microorganism.

One can grow the bacterial strains at a temperature of about 62° C. to about 100° C., specifically the temperature is about 62° C.

One can grow the bacterial strains at a pH from about 5.0 to about 8.0, specifically where the pH is about 7.4.

As described above, medium are currently known that are effective in promoting growth of these microorganisms. Those skilled in the art would know which mediums would be effective in promoting the growth of these microorganisms. In a specific embodiment, applicants used trypticase soy medium.

This invention is illustrated in the Experimental Details section which follows. These sections are set forth to aid in an understanding of the invention but are not intended to, and should not be construed to, limit in any way the invention as set forth in the claims which follow thereafter.

First Series Of Experiments

MATERIALS AND METHODS

Bacterial Strains: Origin of the Isolates.

Strains SH2A and Strain SH2B were isolated from a sample of compost collected in Osaka, Japan.

Culture Methods and Media.

Regular aerobic techniques were used in all experiments. Strains SH2A and SH2B were cultured on trypticase soy medium (BBL) at 64° C.

Sporulation Test.

Nutrient Agar (Oxoid, UK) was used to test for sporulation. The plate was inoculated with an overnight culture and then incubated at 64° C. for up to 5 days to determine the presence of spores.

The heat-resistance of the cultured cells was determined in trypticase soy broth. After overnight incubation at 60° C., 70° C., 80° C., and 90° C. respectively, the viability of the cells was monitored by subculturing on trypticase soy agar plates at 64° C.

Morphological Characteristics.

Morphological properties were determined by phase-contrast microscopy, and scanning electron microscopy.

Analytical Techniques.

Aerobiosis was achieved by growing cultures in the Staphyogram Identification kit (Thermo, Japan). Acid production was tested in the presence of mannose, lactose, maltose, glycerol, salicin, trehalose, sucrose, mannitol, fructose and raffinose. Indole production was tested with Kovacs reagent. Nitrate reduction was tested with Griess's reagent. β-glucosidase, β-glucuronidase, arginine-dehydrase, and urease activity were also determined with the Staphyogram Identification kit. DNAase production was determined by the agar plate method using salmon sperm DNA and assessing halo formation after DNA precipitation with 1.5 N HCl. High salt tolerance by the cells was determined by growth of the bacterial culture in trypticase soy agar plates containing 7.5% NaCl at 64° C. overnight. Kanamycin and ampicillin resistance were measured by growing cells in Muller-Hinton agar plates containing 50 µg of each of these antibiotics at 64° C., overnight. Hemolysis was measured in trypticase soy agar plates containing 5% sheep blood at 64° C. overnight. Gram staining was performed using the standard method.

16S rRNA Sequence Studies.

Purification of genomic DNA, and amplification and purification of the 16S rRNA gene segment from isolate SH2A were performed using commercially available kits (Gene Amp kit, Geneclean spin). The purified PCR product was directly sequenced. Sequencing was performed on an ABI automated DNA sequencer using a Prism dideoxy terminating cycle sequence kit as recommended by the manufacturer (Applied Biosystems, LTD). The primers used for amplification and sequencing are 16SRR I: cag cag ccg cgg taa tac (Seq. I.D. No. I) and 16SRR VIII: gat tag ata ccc tgg ta (Seq. I.D. No. 2). The resulting DNA sequence for the 16S rRNA gene segment (DNA Strider) was aligned with 16S rRNA sequences obtained from the Ribosomal Database Project and from Genbank, and compared. The resulting DNA sequence for the 16S rRNA gene sequences was unique compared to known bacteria (FIG. 1) (Seq. I.D. No. 3).

Biodegradation of the Tuna Fish Head and Extraction of Docosahexanoic Acid (DHA).

One hundred kilogram of frozen tunafish heads (27% DHA) were mixed with a suspension of $1 \times 10^{11}$ cells of Strain SH2A and 10 g of vitamin E and incubated at 75° C., for 4 hours or 8 hours. The biodegraded samples were assayed for DHA. The saponified tunafish oil from each sample was assayed by treating the oil with 4N NaOH-ethylalcohol at 60° C. Free fatty acid was obtained by n-hexane extraction. Analysis of DHA in the fatty samples was performed using gas liquid chromatography (GLC).

Biodegradation of Polychlorobiphenyl (PCB).

Trypticase soy broth containing twenty ppm of each isomeric PCB was inoculated with $1 \times 10^7$ cells/ml of the strain SH2B and was incubated at 64° C. up to 5 days. After incubation, the sample was extracted by n-hexane and analyzed by GLC.

Bacterial Accumulation of Heavy Metal (Cd).

Six μg of Cd $(NO_3)4H_2O$ in trypticase soy broth (2.2 ppm of Cd) was mixed with $1 \times 10^7$ cells/ml of Strain SH2B and incubated at 64° C., for 3 days. After incubation, the sample was centrifuged to pellet the bacterial cells and the supernatant was measured by Cd atomic infrared absorbance.

Plastic Degradation.

One $cm^2$ of polyethylene vinyl sheet was irradiated by UV radiation at 140 nm for 1 hour and incubated in trypticase soy broth with Strain SH2B at 64° C. for 2 days. Scanning electron microscopic analysis was performed on the vinyl surface of the treated samples.

RESULTS

Strains SH2A and SH2B were named Bacillus midousuji after the place at which the bacterial strains were found in composted leaves and branches.

1. Activity in Different Media

The results showed the strains to be gram-positive rods capable of spontaneous spore formation. SH2A produced acid from mannose, maltose, salicin, trehalose, sucrose, mannitol, fructose and raffinose. SH2A was also positive for indole production, nitrate reduction, β-glucosidase, β-glucuronidase, urease, and DNAase activity (Table I).

TABLE I

Characterization Of Activity Of Strains SH2A and SH2B

| Medium containing: | SH2A | SH2B |
|---|---|---|
| 1. Mannose | + | + |
| 2. Lactose | − | − |
| 3. Maltose | + | + |
| 4. Glycerol | − | − |
| 5. Salicin | + | + |
| 6. Voges Proskauel Reaction | − | − |
| 7. Trehalose | + | + |
| 8. Sucrose | + | + |
| 9. Mannitol | + | + |
| 10. Fructose | + | + |
| 11. Raffinose | + | − |
| 12. Nitrate Reduction | + | + |
| 13. β-glucosidase | + | + |
| 14. O-Nitrophenyl G β-galactosidase | − | − |
| 15. β-glucuronidase | + | + |
| 16. Arginine Dehydrogenase | − | − |
| 17. Urease | + | + |

SH2A is sensitive to both kanamycin at concentrations of 50 μg/ml and to ampicillin at concentrations of 50 μg/ml (Table II).

TABLE II

Bacterium Activity In Various Media

| Characteristics studied: | SH2A | SH2B |
|---|---|---|
| 1. Growth in trypticase soy agar containing 5% sheep's blood | + | + |
| 2. Hemolysis activity in trypticase soy agar containing 5% sheep's blood | − | − |
| 3. Dnase activity in agar containing DNA | + | + |
| 4. Growth in trypticase soy agar medium containing 7.5% NaCl | + | + |
| 5. Growth in Muller-Hinton agar containing 50 μg/ml kanamycin | − | + |
| 6. Growth in Muller-Hinton agar containing 50 μg/ml ampicillin | − | − |
| 7. Growth in n agar medium containing X-gal | − | − |

Strain SH2A displays a smooth colony surface on trypticase soy agar and produces a homogeneous suspension during growth in trypticase soy broth.

Another strain, SH2B, was positive for acid production from mannose, maltose, salicin, trehalose, sucrose, mannitol, fructose, and for indole production, nitrate reduction, β-glucosidase, β-glucuronidase, urease, and DNAase activity (Table I).

This strain is resistant to kanamycin at concentrations of 50 μg/ml, but sensitive to ampicillin at concentrations of 50 μg/ml (Table II).

Strain SH2B forms sticky colonies on trypticase soy agar and shows filamentous growth in trypticase soy broth.

Both SH2A and SH2B strains are thermophilic extremophiles and require at least 62° C. to grow.

Strains SH2A and SH2B grew in medium containing 7.5% NaCl. These strains do not reveal hemolytic activity in sheep blood agar plates (Table II).

Comparison of the sequences for the 16S rRNA genes with other bacterial rRNA genes indicated that both strains are new species in the genus Bacillus (FIG. 1).

2. Biodegradation of Tuna Fish Head and Extraction of DHA.

Tunafish heads containing 27% DHA were biodegraded by Strain SH2A. After 4 hour and 8 hour incubation periods, the free DHA concentration increased to 60%.

3. Biodegradation of PCB.

Twenty ppm of PCB was completely degraded by Strain SH2B after 5 days of incubation.

4. Bacterial Accumulation of Heavy Metal (Cd).

Six μg of $Cd(NO_3)4H_2O$ in trypticase soy broth (2.2 ppm of Cd) containing $1 \times 10^7$ cells/ml of Strain SH2B was incubated at 64° C. for 3 days. After the incubation period, the sample was centrifuged and supernatant was analyzed. The supernatant contained 0.036 ppm of Cd concentration after 3 days of incubation (0.016 times dilution).

5. Plastic Degradation.

A one $cm^2$ sample of polyethylene vinyl sheet was irradiated by UV radiation at 140 nm for 1 hour, and incubated in trypticase soy broth with Strain SH2B at 64° C. for 2 days. Scanning electron microscopic analysis showed evidence of biodegradation; the plastic surface contained holes. The control plastic surface (no UV irradiation) remained intact in the absence or presence of bacterial cells. Applicants speculate that the intact plastic is a polycarbohydrate film and that UV irradiation converted the film to a carboxylated film on which the bacterial cells could adhere, grow and cause degradation of the plastic.

Second Series Of Experiments

Bacterial Strains: Origin of the Isolates.

Strains SH2A and Strain SH2B were isolated from a sample of compost collected in Osaka, Japan.

Culture Methods and Media.

Regular aerobic techniques were used in all experiments. Strains SH2A and SH2B were cultured on trypticase soy medium (BBL) at 64° C.

Biodegradation of Squid

One hundred kilogram of squid were mixed with a suspension of cells of Strain SH2A and incubated at 62° C., for 6 hours. The biodegraded samples were assayed for DHA, EPA and PCB and other features, such as fatty acid. Free fatty acid was obtained by n-hexane extraction. Analysis of DHA in the fatty samples was performed using gas liquid chromatography (GLC). Analysis of PCB was also performed using GLC.

RESULTS

The results of the degradation of squid using the bacterial strain SH2A after incubation at 65° C. for 6 hours incubation are shown in Table III.

TABLE III

Degradation of Squid

| FACTOR STUDIED | ACTIVITIES OBSERVED |
| --- | --- |
| Fatty Acid | |
| DNA | 9.89% (Docosahexanoic acid) |
| EPA | 9.24 (EisocaPentanoic acid) |
| Oxidation | 5.20 |
| Ionization | 132.87 |
| Per Oxidation | 0.20 |
| Color (APHA) | 85 |
| Heavy Metal | (atomic flame absorbance) |
| Cadmium | 0 |
| Zinc | 0 |
| Mercury | 0 |
| As | 0 |
| PCB | 0.13 (Gas chromatography) |

CONCLUSION

Biodegradation of Tuna Fish Head and Extraction of DHA.

Squid were biodegraded by Strain SH2A. After a 6 hour incubation period at 65° C., signs of degradation of the squid was observed.

Third Series Of Experiments

Expansion of commercial activity arising from research in molecular and cellular biology, assures fermentation biotechnology of a bright future. In the long term, fermentation of renewable raw materials may replace depleting non-renewable fossil-fuels as a source of bulk chemicals.

Important recent developments in genetic engineering have extended the scope and potential of industrial fermentation technology. By using genetic engineering, one may construct new combinations of inheritable material by inserting the foreign genes into bacteria and other suitable organisms. One of the workhorses of the fermentation industry, Bacillus, may be a suitable bacterial host for such genetic engineering experiments.

In eukaryotic micro-organisms such as Saccharomyces and Aspergillus, protein synthesis and secretion systems are significantly more complex than in prokaryotes, e.g. Bacillus, particularly for producing recombinant non-pharmaceutical products, for example, enzymes.

Proteins and peptides, the translation products of structural genes, are the first obvious targets using recombinant DNA technology. In the future, it may be possible to manipulate primary and secondary metabolic systems to improve metabolite production by genetic engineering of key enzymes.

Thermophilic Bacillus producing high-temperature-stable enzymes, which have the ability to degrade substrates up to 100° C., have not only streamlined substrate-hydrolysis processes but have also created an impetus to isolate or construct other enzymes with highly stable properties.

Bacteria can express proteins at high levels. Gram-negative bacteria are in general not good extracellular protein secretors; gram-positive bacteria are significantly better at secreting extracellular proteins. Therefore, thermophilic Bacillus, such as SH2A and SH2B, may be a suitable producer of industrial enzymes.

Applicants will develop improvements of the bacterial strains SH2A and SH2B, possibly by DNA recombination, that will provide potent rapidly growing, but safe and effective recombinant bacteria that can be used for multiple purposes. For example, applicants plan to introduce genes which further enhances lipid, protein, carbohydrate, or fiber degradation. Lipids are an ideal target because the materials are easily collected from waste and requires only a minor handling process. The processed lipid can then be degraded in waste by bacterium.

What is claimed is:

1. A biologically pure culture of a microorganism capable of degrading organic material designated SH2A and deposited under ATCC Accession No. 55926, or a mutant derived therefrom having degrading activity of said microorganism.

2. A biologically pure culture of a microorganism capable of degrading organic material designated SH2B and deposited under ATCC Accession No. 202050, or a mutant derived therefrom having degrading activity of said microorganism.

3. A method of degrading an organic material which comprises treating the organic material with an effective, degrading amount of a microorganism designated SH2A and deposited under ATCC Accession No. 55926, or a mutant derived therefrom which retains the degrading activity thereof, so as to thereby degrade the material.

4. A method of degrading an organic material which comprises treating the organic material with an effective, degrading amount of a microorganism designated SH2B and deposited under ATCC Accession No. 202050, or a mutant derived therefrom which retains the degrading activity thereof, so as to thereby degrade the material.

5. The method of claim 4, wherein the organic material is a plastic material.

6. The method of claim 5, wherein the plastic material is polyethylene.

7. The method of claim 6, wherein the polyethylene is irradiated prior to treatment with the microorganism.

8. The method of claim 7, wherein the irradiation comprises exposing the polyethylene to ultra-violet light.

9. The method of claim 3 or 4, wherein the organic material comprises a protein.

10. The method of claim 3 or 4, wherein the organic material comprises a sugar.

11. The method of claim 3 or 4, wherein the organic material comprises an amino acid.

12. The method of claim 3 or 4, wherein the organic material comprises a nucleic acid molecule.

13. The method of claim 12, wherein the nucleic acid molecule comprises a deoxyribonucleic acid molecule.

14. The method of claim 3, wherein the organic material comprises tunafish heads.

15. The method of claim 3, wherein the organic material comprises squid.

16. The method of claim 3 or 4, wherein the treatment is effected at a temperature from about 62° C. to about 100° C.

17. The method of claim 16, wherein the temperature is about 62° C.

18. The method of claim 3 or 4, wherein the treatment is effected at a pH at about 5.0 to about 8.0.

19. The method of claim 18, wherein the pH is about 7.4.

20. The method of claim 3 or 4, wherein the treatment is effected in an a erobic environment.

21. A method for growing a microorganism designated SH2A and deposited under ATCC Accession No. 55926, or a mutant derived therefrom, which comprises culturing the microorganism at a temperature and in a medium effective to promote growth of the microorganism.

22. A method for growing a microorganism designated SH2B and deposited under ATCC Accession No. 202050, or a mutant derived therefrom, which comprises culturing the microorganism at a temperature and in a medium effective to promote growth of the microorganism.

23. The method of claim 21 or 22, wherein the temperature is about 62° C. to about 100° C.

24. The method of claim 23, wherein the temperature is about 62° C.

25. The method of claim 21 or 22, wherein culturing is at a pH of about 5.0 to about 8.0.

26. The method of claim 25, wherein the pH is at about 7.4.

* * * * *